United States Patent

Conero et al.

[11] Patent Number: 5,545,140
[45] Date of Patent: Aug. 13, 1996

[54] SYRINGE PLUNGER DRIVER

[75] Inventors: Ronald S. Conero, San Diego; Stephen H. O'Leary, Encinitas, both of Calif.

[73] Assignee: IVAC Corporation, San Diego, Calif.

[21] Appl. No.: 270,393

[22] Filed: Jul. 5, 1994

Related U.S. Application Data

[63] Continuation of Ser. No. 97,575, Jul. 26, 1993, abandoned, which is a continuation of Ser. No. 704,322, May 23, 1991, abandoned.

[51] Int. Cl.⁶ .................................................. A61M 5/20
[52] U.S. Cl. ........................ 604/154; 604/67; 128/DIG. 1
[58] Field of Search ................................ 604/65, 67, 151, 604/154, 155, 245; 128/DIG. 1, DIG. 12, DIG. 13

[56] References Cited

U.S. PATENT DOCUMENTS

| | | | |
|---|---|---|---|
| 3,235,220 | 2/1966 | Rantsch et al. | |
| 3,757,591 | 9/1973 | Taylor. | |
| 3,842,690 | 10/1974 | Gulick. | |
| 3,858,581 | 1/1975 | Kamen. | |
| 3,886,938 | 6/1975 | Szabo et al. | |
| 4,023,431 | 5/1977 | Pavlas. | |
| 4,125,049 | 11/1978 | Price, Jr. | |
| 4,191,187 | 3/1980 | Wright. | |
| 4,424,720 | 1/1984 | Bucchianeri | 74/89 |
| 4,435,173 | 3/1984 | Siposs et al. | |
| 4,465,474 | 8/1984 | Mardorf. | |
| 4,544,369 | 10/1985 | Skakoon et al. | |
| 4,560,979 | 12/1985 | Rosskopf. | |
| 4,685,903 | 8/1987 | Cable et al. | |
| 4,731,058 | 3/1988 | Doan | 604/155 |
| 4,767,406 | 8/1988 | Wadham et al. | 604/155 |
| 4,804,368 | 2/1989 | Skakoon et al. | 604/155 |
| 4,838,857 | 6/1989 | Strowe et al. | 604/67 |
| 4,908,017 | 3/1990 | Howson et al. | |
| 4,919,650 | 4/1990 | Feingold et al. | |
| 4,931,041 | 6/1990 | Faeser. | |
| 4,952,205 | 8/1990 | Mauerer et al. | |
| 4,959,056 | 9/1990 | Dombrowski et al. | |
| 4,976,696 | 12/1990 | Sanderson et al. | 604/154 |
| 4,988,337 | 1/1991 | Ito. | |
| 5,006,112 | 4/1991 | Metzner. | |
| 5,034,004 | 7/1991 | Crankshaw | 604/154 |
| 5,176,646 | 1/1993 | Kuroda | 604/154 |
| 5,236,416 | 8/1993 | McDaniel et al. | 604/67 |
| 5,259,732 | 11/1993 | Stem | 417/63 |
| 5,295,967 | 3/1994 | Rondelet et al. | 604/154 |

FOREIGN PATENT DOCUMENTS

| | | |
|---|---|---|
| 0354852 | 2/1990 | European Pat. Off. |
| 3314664C2 | 2/1985 | Germany. |
| 1475673A1 | 4/1989 | U.S.S.R. |
| WO90/10468 | 9/1990 | WIPO. |

*Primary Examiner*—Corrine M. McDermott
*Attorney, Agent, or Firm*—Fulwinder Patton Lee and Utecht

[57] ABSTRACT

A plunger driver system which engages a plurality of different sizes of syringes. A pushing surface includes a detector to determine syringe plunger presence. In the event that the plunger is not present and the pump is operating, a processor provides an alarm and may stop the pump motor. Arms retain the plunger flange in a fixed position in relation to the plunger driver. The arms have anti-siphon flanges to prevent too rapid movement of the plunger into the syringe barrel. A shelf for opposing downward movement of the syringe plunger and a ramp to guide the syringe plunger into position in relation to the plunger driver are included in the plunger driver. A cradle for containing all sizes of syringe barrels yet aligning the syringes with the plunger driver is included with a clamp to hold the syringe barrel in position in the cradle. The detector button includes a bevel at its top edge to facilitate loading the plunger in the driver. The plunger driver arms are biased independently from the screw drive disengagement mechanism. A ramp is also formed with the shelf to assist in guiding the syringe plunger into position during syringe installation.

25 Claims, 5 Drawing Sheets

SYRINGE PLUNGER DRIVER

BACKGROUND

This is a continuation, of application Ser. No. 08/097,575 filed Jul. 26, 1993, now abandoned, which is a continuation of application Ser. No. 07/704,322 filed May 23, 1991 now abandoned.

The invention is related generally to linear drive mechanisms, and more particularly, to a system for driving the plunger of a syringe.

The infusion of fluids such as parenteral fluids into the human body is accomplished in many cases by means of a syringe pump having a lead screw and a screw drive mechanism which translates the rotational motion of the lead screw into linear motion. A syringe plunger driver is connected to the screw drive mechanism for connecting the linear motion of the screw drive mechanism to the syringe plunger to empty the syringe.

Because syringes are of different sizes and are filled to different levels with infusion fluids, the extension of the plunger from the syringe barrel will differ from syringe to syringe. Many screw drive mechanisms include a disengagement mechanism which the operator uses to disengage the lead screw drive mechanism from the lead screw threads. Once disengaged, the operator may move the plunger driver along the lead screw to the position of the extended syringe plunger, and then engage both the syringe plunger with the plunger driver and the lead screw drive mechanism with the threads of the lead screw at the new position. It is desirable that this disengagement mechanism and this plunger driver mechanism be easy to use to facilitate operator usage of the pump.

As is well known, syringes vary in size among manufacturers. Even syringes designed to contain the same quantity of fluid can vary substantially in outer dimensions of both length and diameter from manufacturer to manufacturer. In some prior pumps, only a single syringe from a single manufacturer could be used, thereby greatly restricting the usefulness of the pump. When that particular syringe type was not available, the pump could not be used. It would be desirable to provide a syringe pump which is capable of accepting different capacity syringes as well as accepting syringes made by different manufacturers. This has been a formidable obstacle in the past because not only can syringe barrel diameter vary from syringe to syringe, but also the barrel flange size, the length of the syringe barrel, the plunger length and the plunger flange diameter and thickness can all vary. All of these physical variables would have to be considered when designing a plunger driver system for a syringe pump if that pump is to be capable of handling syringes of differing capacities from a variety of manufacturers.

In a syringe pump plunger driver, the driver typically engages the plunger flange and holds that flange in a fixed relationship with a pushing surface which is part of the plunger driver. The pushing surface contacts the plunger flange and applies force to move the plunger flange into the syringe to expel the syringe contents. The plunger driver typically includes a retainer structure which operates as an anti-siphon feature to prevent the plunger from moving into the barrel and emptying the syringe under a negative pressure condition at a rate in excess of the programmed movement rate of the pushing surface. The plunger driver should also be designed so that it does not impart pressure against the syringe in a direction which may cause the plunger to dislodge from the plunger driver. Additionally, if the plunger were to dislodge from the plunger driver during pump operation or not be present for other reasons, it would be desirable to indicate this event by providing an alarm to the operator and if desired, stopping the rotation of the lead screw.

Some prior syringe pumps have coupled the lead screw disengagement apparatus to the part of the plunger driver which holds the syringe plunger in a fixed position relative to the plunger driver. Thus, the pump operator need only operate one mechanism to both move the plunger driver and engage it with the flange of the new syringe. This feature contributes to ease of use of the pump. In a syringe pump where different sizes of plunger flanges may be used, the screw disengagement system and the plunger driver interface with the plunger should be designed to work equally well with all such syringe sizes. That is, the screw drive mechanism should not be affected by dimensional changes of the plunger.

In the case where a syringe pump is to accommodate a wide variety of different syringe sizes, a plunger driver system is needed which will precisely hold each syringe in correct alignment with the pushing surface of the plunger driver so that regardless of size, the alignment of the syringe with the plunger driver will be correct. The system must also assure that the plunger will be firmly held in the plunger driver and that the plunger detector system will detect the presence and absence of each of the different sized syringes and provide an alarm in the case of a dislodged or absent plunger. Additionally, it would be desirable if such a system were easy to use.

Hence, those skilled in the art have recognized a need for a plunger driver system which is capable of handling different sizes of syringes while still presenting a relatively easy system to use to the operator of the pump. Such a system should provide a mechanism to align, firmly engage and detect the presence of the plunger of each of the syringes specified for the pump. The invention fulfills these needs.

SUMMARY OF THE INVENTION

The present invention provides a syringe plunger driver system for engaging syringes of different sizes with a single plunger driver. A syringe barrel cradle is located on the pump body to align the syringe in use with the movable plunger driver mechanism and hold the syringe barrel in a fixed position. The cradle is shaped to accept all of the syringes specified for the pump and align the plunger of each of these syringes with the pushing surface of the plunger driver. Also included with the cradle is a syringe barrel clamp to securely hold the syringe in position in the cradle. The clamp is mounted and pivoted above the barrel central axis of the largest diameter barrel to impart a substantially downward force to the syringe being used to firmly hold the syringe in position in the cradle regardless of syringe size.

The pushing surface of the plunger driver includes a plunger detector located in such a position that it is effective in detecting the presence of the plungers of all of the different syringes specified for the pump. A self-adjusting plunger retainer grasps the plunger flange of the syringe and holds it in a fixed position in relation to the pushing surface of the plunger driver. The plunger retainer includes an anti-siphon feature to oppose forward movement of the plunger which would exceed the movement of the plunger driver. A shelf is mounted on the bottom of the pushing surface for opposing downward movement of the syringe plunger and a ramp is mounted to guide the plunger flange into the correct alignment with the pushing surface of the plunger driver during installation of the syringe.

The range of detection of the plunger detector is selected to accommodate all of the syringes specified with the pump, some of which have substantially thinner plunger flanges than others. In the event that the pump is operating and the plunger detector senses that no plunger is present, a detector signal is provided to a processor and an alarm is given. In one embodiment, the pump motor is stopped also. In one embodiment, the detector uses a spring-loaded button to make contact with the syringe plunger flange and that button is beveled at its top surface to facilitate loading the plunger into the plunger driver system when loading the syringe.

The plunger retainer is self-adjusting to all of the sizes of plunger flanges of the syringes specified for the pump. In one embodiment, a pair of pivoted arms is used to contact the plunger flange and hold it in position. The arms are shaped to apply lateral force to the flange or a slight downward force. Each of the arms includes an anti-siphon flange to oppose forward movement of the plunger flange in excess of that provided by the plunger driver.

The plunger retainer is coupled to a single disengagement lever which functions to both disengage the screw drive mechanism from the lead screw and disengage the plunger retainer from the syringe plunger. When moved to a first position, the disengagement lever functions to disengage the screw drive mechanism from the lead screw, such as by moving the split nut away from the lead screw threads so that no contact is now made, and to open the plunger retainer to allow insertion or removal of a plunger flange. When the plunger driver has been moved to the desired position along the lead screw and the plunger flange of the new syringe contacts the plunger driver pushing surface and detector button, the lever is released and the plunger retainer contacts the plunger and the screw drive mechanism reengages the threads of the lead screw. The plunger retainer includes a biasing apparatus which biases the retainer against the circumference of the plunger flange. In accordance with the invention, this biasing apparatus is independent from the biasing apparatus used to bias the screw drive mechanism into contact with the lead screw. Thus, different sizes of plunger flanges do not interfere with the engagement of the screw drive mechanism with the threads of the lead screw.

In the case of small plungers specified for the pump, the plunger retainer may apply a limited downward force to the plunger. However, the shelf is mounted to oppose such downward force and assist in holding the plunger in the correct position at the pushing surface.

Other aspects and advantages of the invention will become apparent from the following detailed description and the accompanying drawings, illustrating by way of example the features of the invention.

DETAILED DESCRIPTION OF THE PREFERRED EMBODIMENTS

Figure 1:
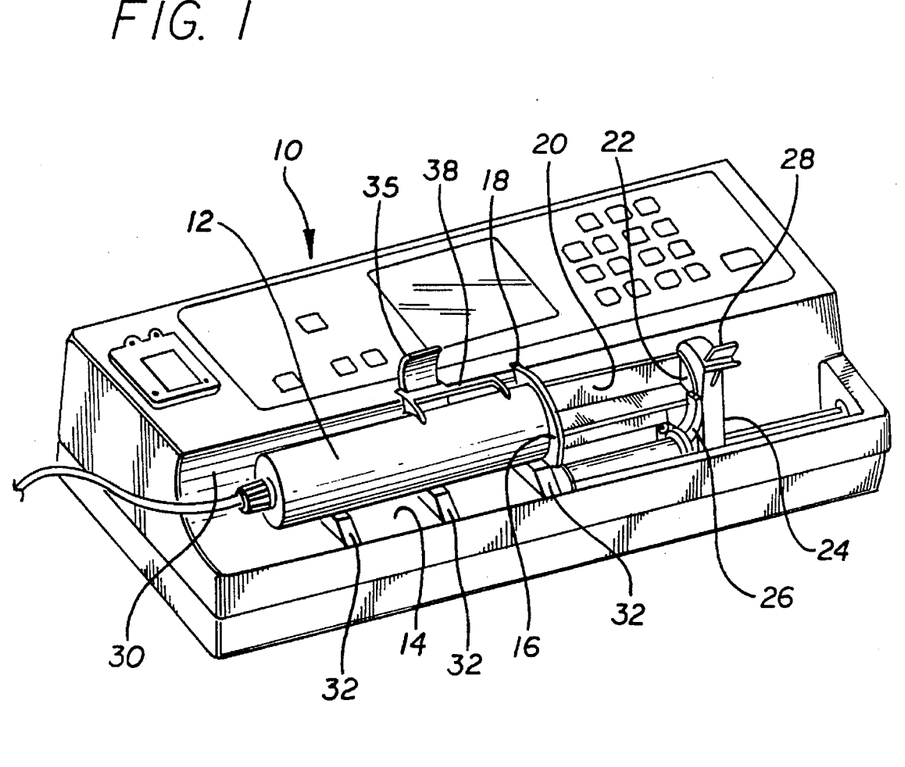
FIG. 1 is a perspective view of a syringe pump showing a plunger driver system in accordance with the principles of the invention.

Referring now to the drawings with more particularity, wherein like reference numerals designate like or corresponding elements among the several views, there is shown in FIG. 1 a perspective view of a syringe pump 10 having a plunger driver system in accordance with the principles of the invention. A syringe 12 is mounted in a syringe cradle 14. The syringe barrel flange 16 is located in a barrel flange groove 18 to immobilize the syringe barrel from longitudinal movement during movement of the syringe plunger 20. The plunger flange 22 is held in the plunger driver 24 with a pair of plunger retaining arms 26, one of which is shown in FIG. 1. A disengagement lever 28 is used to disengage the plunger driver 24 from the lead screw (not shown) to allow removal and insertion of a syringe plunger flange 22.

Figure 2:
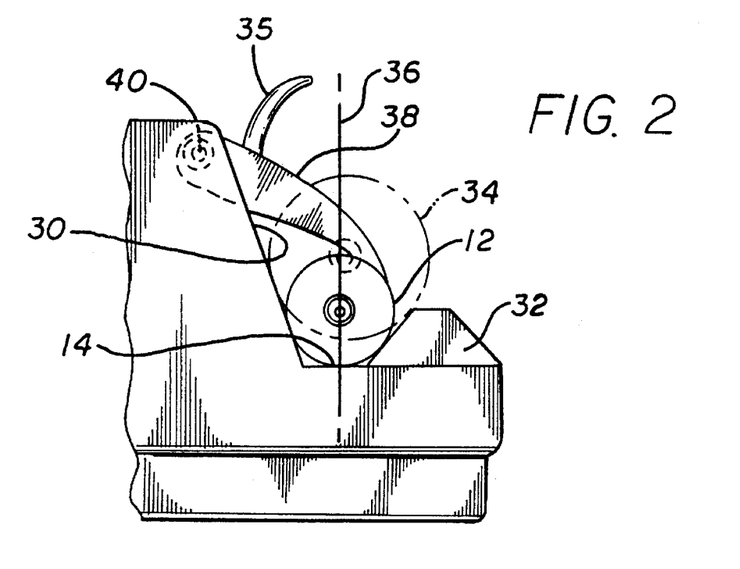
FIG. 2 is a view of a cradle and barrel clamp in the syringe pump of FIG. 1.

Referring now to FIGS. 1 and 2, the cradle 14 has a shape such that it will accept the barrels of all of the syringes 12 specified for the pump 10 and align them such that their plunger flanges will contact the plunger driver in a predetermined area on that plunger driver. The cradle has a sloping body side 30 formed as part of the pump 10 body and three barrel retainers 32 which support the barrel and retain it from rolling out of the cradle 14. The body side 30 and the barrel retainers 32 form a V-shape with a 96° included angle. The syringes 12 inserted in the cradle 14 will all align with the plunger driver 24 within a particular vertical range. The points where the longitudinal center lines of the syringes intersect the plunger driver will change according to the size of the syringe but only in the vertical direction along the single line 36 as shown in FIG. 2.

In FIG. 2, a first syringe 12 is shown in solid lines and a second syringe 34 is shown in dashed lines. By means of the particular shape of the body slope 30 and the retainers 32, the longitudinal centerlines of all syringes will align along the vertical centerline 36 even though the syringes will rest in different positions in the cradle 14. The smaller syringes will fit farther towards the bottom of the cradle as shown with syringe 12 and the larger syringes will be higher in the cradle 14 as shown with syringe 34. However, the longitudinal centerlines of all of the syringes will fall on the vertical position centerline 36 as shown in FIG. 2.

A syringe barrel clamp 38 applies downward pressure on the syringe barrel 12 as shown in FIGS. 1 and 2. The clamp 38 includes a coil spring 40 in this embodiment which is coupled to the clamp's pivot point. A thumb lever 35 is provided for opening the clamp to permit replacement of the syringe 12. The clamp 38 is mounted above the syringe position in the pump so that a downward force will be applied to the syringe barrel to retain the syringe in the cradle 14 regardless of syringe size.

Figure 3:
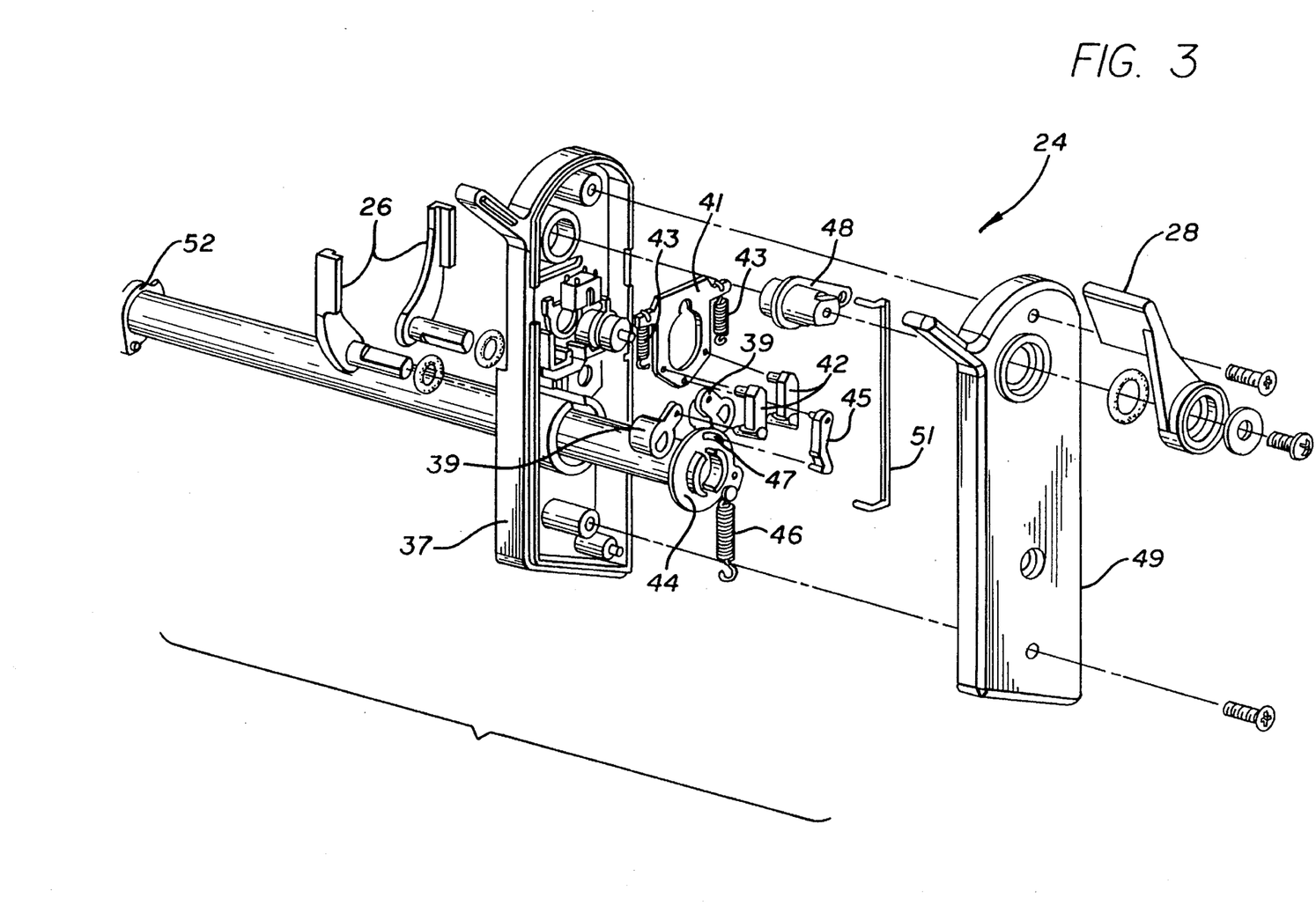
FIG. 3 is an exploded view of a plunger driver incorporating the principles of one aspect of the invention, showing the plunger retainer arms, the activating lever, and the independent biasing means of those arms.

Referring now to FIG. 3, an exploded view of the parts of the plunger driver 24 is presented. The plunger driver 24 includes a pair of retaining arms 26 used to grip the plunger flange of the inserted syringe (not shown). These arms are individually pivoted in this embodiment and are spring biased to close toward each other. Each arm 26 is located through the front housing 37 into respective inner crank arms 39 which are connected to the sliding plate 41 with activating links 42. The sliding plate 41 is spring biased 43 downward and operates to bias the arms toward each other. The sliding plate 41 is connected to the tube crank 44 by another activating link 45. The tube crank 44 rotates and is spring biased 46. At the other end, the tube crank 44 is connected to the split nut mechanism 52 to engage and disengage it from the lead screw by opening and closing it respectively. The spring bias 46 operates to bias the split nut closed and into engagement with the lead screw.

Thus there are two independent biasing systems. The first 43 operates on the retaining arms 26 while the second 46 operates on the split nut. The slot 47 in the tube crank 44 allows the arms 26 a range of movement independent from the split nut. The arms may therefore engage plungers of different diameters and because of the slot 47, are not forced to return to the position closest to each other. Thus, in the case where the arms 26 must grasp a large plunger flange and do not move back together to a closer position as they would if they were grasping a small plunger flange, the amount of movement of the split nut is unaffected. This independence of movement allows for a multiple syringe handling capability of the plunger driver system in accordance with the invention.

Although there are two independent biasing systems, there is a single activating lever 28. The connecting link 51 is connected between the tube crank 44 and the crank arm 48. The crank arm is connected to the lever 28 through the rear housing 49 and will rotate in response to lever 28 movement. The lever movement will thus cause rotation of the tube crank 44 which in turn will cause movement of both the split nut and the retaining arms 26. Moving the lever 28 downward causes the arms to open and the split nut to open.

Figure 4:
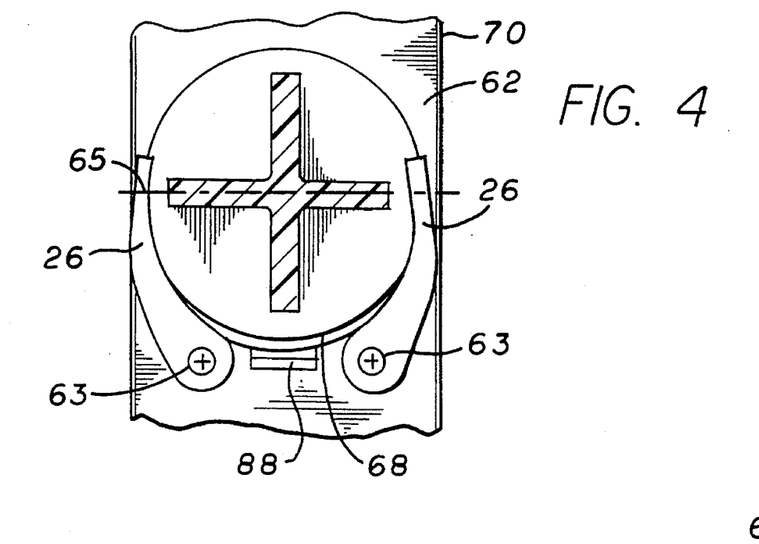
FIG. 4 is a view of the retainer arms grasping a plunger flange of the largest syringe specified for the pump in accordance with the invention.
Figure 5:
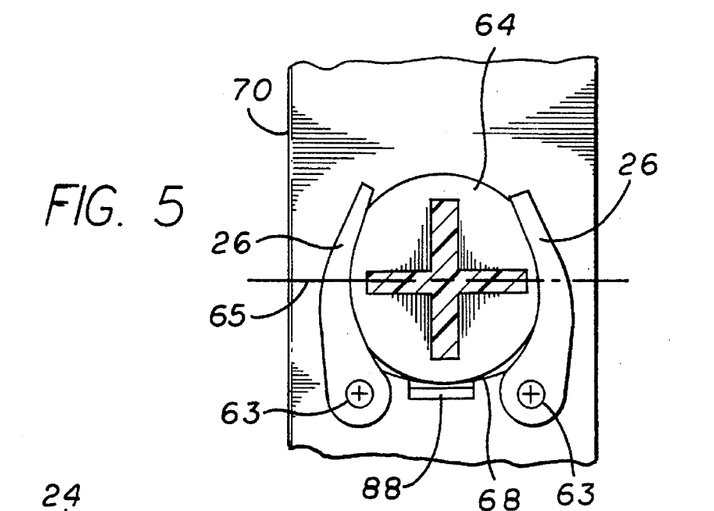
FIG. 5 is a view of the retainer arms grasping a plunger flange of the smallest syringe specified for the pump in accordance with the invention.

Referring now to FIGS. 4 and 5, end views of the operation of the arms is presented where, in FIG. 4, arms 26 are engaging a first plunger flange 62 which is large. In FIG. 5, the arms 26 are engaging a second plunger flange 64 which is small. The arms 26 are located and pivoted about axes 63 such that they will contact the largest plunger specified in the pump at points approximately on or above the lateral centerline 65 of the plunger flange. This will result in the application of a lateral force towards the center of the flange and possibly a slight downward force.

In FIG. 5, the arms 26 are shown engaging the smallest plunger flange 64 specified for the pump and they engage the flange 64 higher on the flange than they did with the larger flange 62. Thus, some downward force is imparted; however, a shelf 68 is included to oppose the downward force of the arms 26 and hold the plunger flange 64 fixed in position in relation to the plunger driver 24. As shown in FIG. 4, the larger plunger flange 62 is not resting on the shelf 68 during operation but may make contact with the shelf during syringe installation. The smaller plunger flange 64 does touch the shelf 68 and rests on it as part of the plunger driver system. The high contacting points of the arms on the small flange 64 do not apply an angular force on the syringe barrel 12 because the cradle is formed so that the smaller syringe barrels specified for the pump are positioned lower and their plunger flanges are meant to rest on the shelf 68.

Figure 6:
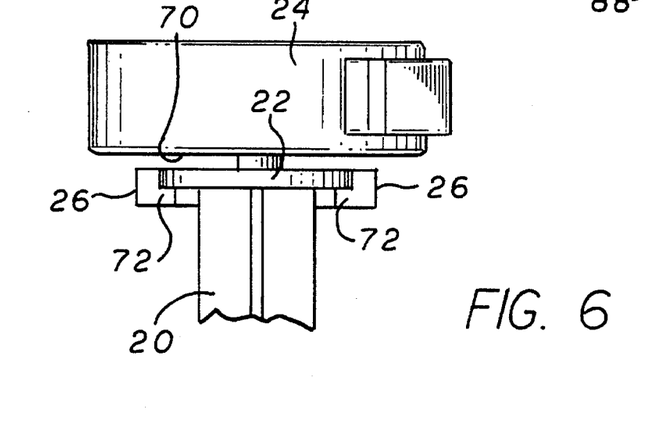
FIG. 6 is a top view of FIG. 4 showing the arms grasping the plunger flange and the anti-siphoning flanges of the arms.

Referring now to FIG. 6, a top view of the engagement of the arms 26 with the plunger flange 22 is shown (the shelf has been removed for clarity). The plunger flange is not resting against the pushing surface 70 of the plunger driver 24 but presently is between the anti-siphon flanges 72 of the arms 26 and the pushing surface 70. The arms 26 are contacting the flange 22 in a lateral direction. If the syringe should be subject to a siphoning action which would tend to pull the plunger into the syringe at a faster rate than programmed into the pump 10, the anti-siphon flanges 72 of the arms 26 will restrain the plunger flange 22 from such movement and prevent emptying the syringe in an uncontrolled manner. When operating in the normal mode, the plunger driver 24 will move forward until the pushing surface 70 contacts the plunger and will then push the plunger into the syringe to expel the contents of the syringe at the programmed rate. The barrel of the syringe is held stationary by disposing the barrel flange in the flange groove as shown in FIG. 1, and the plunger can move relative to the barrel.

Figure 7:
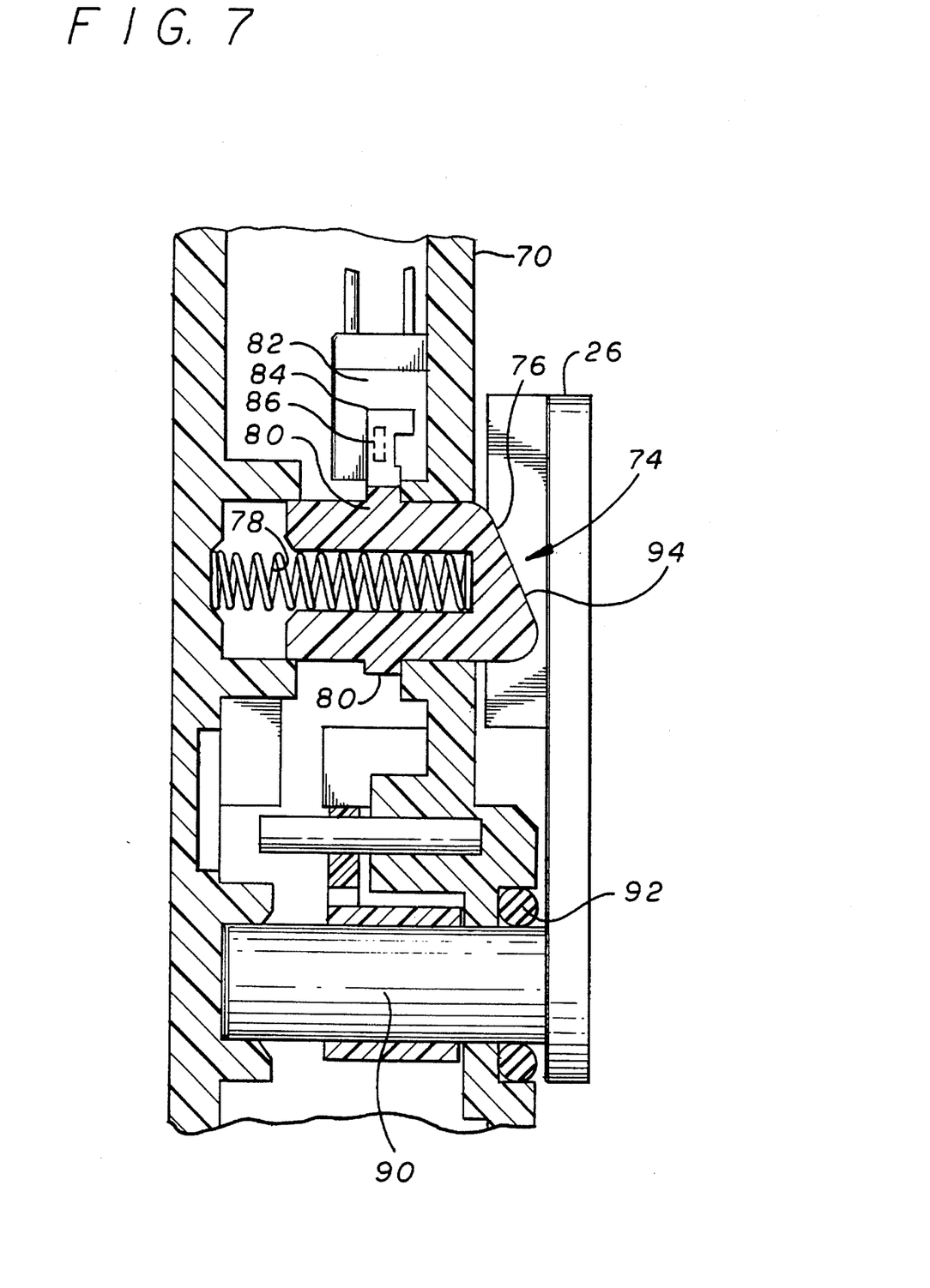
FIG. 7 is a partially cutaway side view of a plunger flange detector system in accordance with the invention showing the detector button in an extended position.
Figure 8:
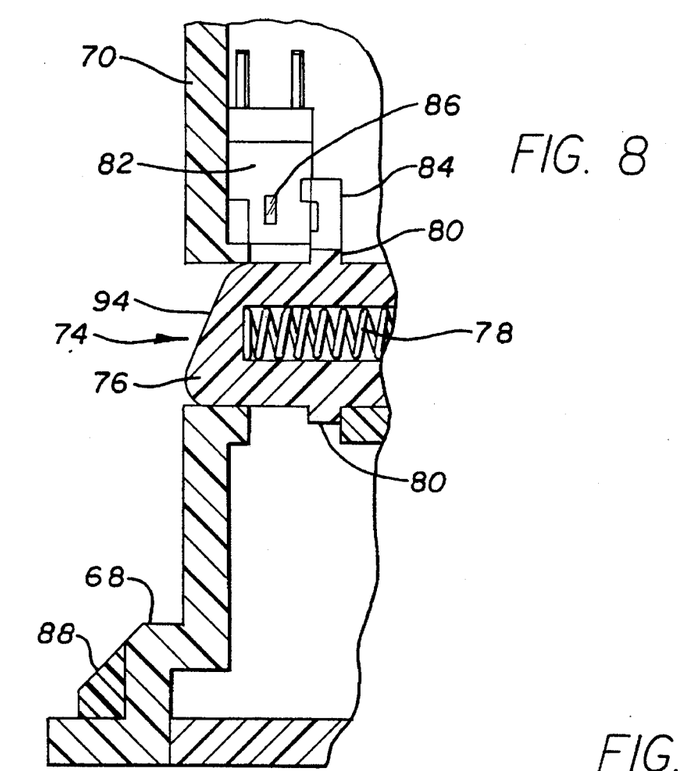
FIG. 8 is a side view, opposite of that of FIG. 7, showing the detector button in a depressed position as it would be if a plunger flange were present and showing the shelf and ramp.

Referring now to FIGS. 7 and 8, a plunger detector 74 is shown. In FIG. 7, the button 76 forming part of the plunger detector 74 is shown in the extended position and in FIG. 8, it is shown in the fully depressed position. A spring 78 is used to bias the detector button 76 outward and an annular stop flange 80 has been formed around the circumference of the button 76 to restrict its forward and rearward movement. An optical sensor 82 determines the presence and absence of a syringe plunger flange at the plunger driver 24 by monitoring the position of the button 76. The button 76 includes a flag 84 on its upper surface for interrupting the beam of the optical sensor 82, which in the cases of FIGS. 7 and 8, would be in the direction out of and into (perpendicular to) the paper. In FIG. 7, the button 76 is completely forward indicating the absence of a plunger flange and the flag 84 is interrupting the optical beam 86 of the optical sensor 82. In FIG. 8, the button 76 is depressed as it would be when pushing against an installed plunger and the flag 84 does not interrupt the beam 86 thus indicating the presence of a plunger flange.

The range of movement of the button 76 and the size of its flag 84 are selected to accommodate a large range of thicknesses of plunger flanges. Typically, thicker flanges are associated with larger syringes and thinner flanges are associated with smaller syringes. In accordance with the invention, the detector is designed to detect all syringes specified for the pump. Thus beam 86 is located so that it will not be interrupted when the button moves out farther to detect small syringes.

Figure 9:
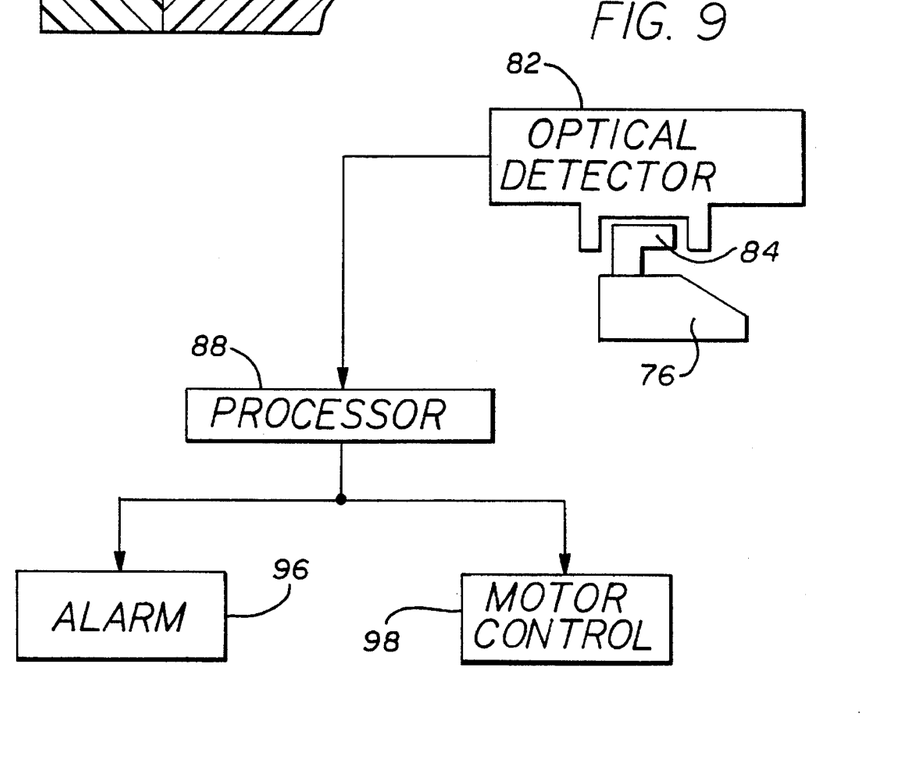
FIG. 9 is a block diagram showing the processing of the plunger detector signal for alarms and motor control.

In one embodiment shown in FIG. 9, the optical sensor 82 signal is connected to a processor 88 which determines from the signal whether a plunger is present. If the pump is in operation and the signal indicates that the plunger is not present, the processor issues an alarm 96 and provides a signal to the motor control 98 to stop the motor.

By arranging the flag 84 as shown in FIGS. 7 and 8, the processor 88 can check the optical beam detector 82 by pulsing the emitter of the detector "on" and looking for a response by the sensor part of the detector. If the pulse is not detected, the processor 88 determines that the detector 82 has failed and the pump enters an alarm state. This arrangement assures that a failed detector 82 does not result in a failure of the system to detect a plunger 20 which has become dislodged from the plunger driver 24.

Another feature shown in FIGS. 7 and 8 is the bevel 94 formed into the top of the button 76. This bevel aids in syringe insertion into the pump 10 by allowing vertical motion during installation. The syringe plunger flange would strike the bevel 94 causing the button 76 to depress somewhat while the syringe is being loaded. Without the beveled surface 94 formed on the button, the syringe would have to be loaded horizontally into the plunger driver 14. With the bevel, the syringe may be loaded either horizontally or vertically thus making operator use of the pump easier.

Also shown in FIG. 8 is the shelf 68 for use particularly with the smaller syringes having small plunger flanges. Associated with the shelf 68 is a ramp 88 for guiding the plunger flanges into the shelf 68 and to the pushing surface 70. A front view of the ramp 88 is shown in FIG. 4. When installing syringes, the plunger may sometimes be oriented such that it is too low in relation to the pushing surface 70 but upon contacting the ramp 88, the plunger flange will be guided into the correct, higher position. This results in easier operation of the pump.

Also shown in FIG. 7 is a single arm 26 with its pivot pin 90 and an O-ring seal 92 surrounding the pin 90.

From the foregoing, it will be appreciated that the plunger driver system in accordance with the principles of the invention provides a versatile system to accept various sizes of syringes and results in easier pump operation.

Although specific embodiments of the invention have been described and illustrated it is clear that the invention is susceptible to numerous modifications and embodiments within the ability of those skilled in the art, and without the exercise of the inventive faculty. Thus, it should be understood that various changes in form, detail and application of the present invention may be made without departing from the spirit and scope of the invention.

We claim:

1. A plunger driver system for engaging selected plungers of syringes of different sizes, each plunger moveable in a syringe barrel and each plunger having a plunger flange with an inner side facing the syringe barrel and an outer side, the plunger driver system moving the plunger into the syringe barrel in an operation mode, the plunger driver system comprising:

a pushing surface adapted to press against the outer side of the plunger flange to move the plunger into the barrel of the syringe during the operation mode;

a plunger retainer adapted to engage the inner side of the plunger flange and physically retain the flange within a predetermined distance from the pushing surface;

a detector coupled to the pushing surface to detect the presence of the plunger flange within the predetermined distance between the pushing surface and the plunger retainer during the operation mode and to provide a detector signal indicating the presence of the plunger, the detector having a detection range large enough to detect the presence of all of the plunger flanges of the different sizes when located between the pushing surface and the plunger retainer;

a spring coupled to the plunger retainer to bias the plunger retainer into contact with the plunger flange; and a processor which receives the detector signal and monitors the detector signal during the operation mode and provides an alarm in the event that the detector signal indicates a syringe plunger not present during the operation mode.

2. The system of claim 1 wherein the plunger flange detector comprises:

a button mounted in the pushing surface;

a spring which biases the button outward into contact with the plunger flange; and a sensor positioned to detect the position of the button and thereby determine the presence of a plunger flange.

3. The system of claim 2 wherein the button comprises a beveled top surface.

4. The plunger driver system of claim 2:

wherein the button comprises a sensing flag moving with the button and movable to a first position in response to a plunger flange being located between the pushing surface and the plunger retainer and movable to a second position when no plunger flange is located between the pushing surface and the plunger retainer;

further comprising a detecting device responsive to the position of the flag to provide the detector signal indicating the position of the flag;

wherein the detecting device is mounted at the second position of the flag and during the operation mode, the processor tests the detecting device for correct operation thereby verifying that the detecting device has not failed.

5. The plunger driver system of claim 4 wherein the detecting device provides an optical beam and is mounted so that when the flag is in the first flag position, the flag does not break the optical beam;

wherein the processor pulses the optical beam when the flag is in the first flag position and provides an alarm if the detecting device does not detect the pulsed optical beam.

6. The system of claim 1 wherein:

the pushing surface comprises a shelf for receiving the plunger flanges; and the plunger retainer applies a downward force to plunger flanges in the direction of the shelf.

7. The system of claim 1 further comprising a ramp disposed adjacent the bottom of the pushing surface which engages the plunger to guide it into a desired position on the pushing surface.

8. The system of claim 1 wherein:

the pushing surface comprises a shelf for receiving the plunger flanges;

the plunger retainer applies a downward force to plunger flanges in the direction of the shelf; and further comprising a ramp disposed adjacent the bottom of the pushing surface which engages the plunger to guide it into a desired position on the pushing surface.

9. The plunger driver system of claim 1 further for use with a lead screw driving mechanism which comprises a lead screw, a driver device coupled to the lead screw for movement along the lead screw in response to rotary motion of the lead screw, and a bias mechanism for biasing the driver device into contact with the lead screw, wherein the plunger driver system is connected to the lead screw driving mechanism wherein:

the plunger retainer bias spring is independent from the screw drive bias mechanism.

10. The system of claim 9 further comprising an activating lever which is connected to oppose the bias mechanism of the screw drive mechanism and the lever is also connected to the plunger retainer to disengage the plunger retainer from the plunger flange.

11. The plunger driver system of claim 1 wherein the processor controls the pushing surface to stop pressing against the outer side of the plunger flange upon the processor providing an alarm.

12. The plunger driver system of claim 1 wherein the detector comprises:
   a contact device mounted to the pushing surface for movement therewith, said contact device movable to a first contact position in contact with a plunger flange in response to said plunger flange being located between the pushing surface and the plunger retainer and movable to a second noncontact position when no plunger flange is located between the pushing surface and the plunger retainer;
   a flag mounted to the contact device and moving therewith, the flag movable to a first flag position in response to the contact device being located in the first contact position and a second flag position in response to the contact device being located in the second noncontact position; and
   wherein the detector comprises a detecting device responsive to the position of the flag to provide the detector signal that indicates the position of the flag; and
   wherein the detecting device is mounted at the second flag position of the flag and during the operation mode, the processor tests the detecting device for correct operation thereby verifying that the detecting device has not failed.

13. The plunger driver system of claim 12 wherein the detecting device provides an optical beam and is mounted so that when the flag is in the first flag position, the flag does not break the optical beam;
   wherein the processor pulses the optical beam when the flag is in the first flag position and provides an alarm if the detecting device does not detect the pulsed optical beam.

14. A plunger driver system for engaging plungers of different sizes, each plunger having a plunger flange, the plunger driver system comprising:
   a pushing Surface adapted to press against the plunger flange to move it in a first direction;
   a plunger retainer adapted to engage the plunger flange applying lateral force thereto and retaining the flange within a predetermined distance from the pushing surface, the retainer also adjusting itself to the size of the flange, wherein the plunger retainer comprises a pair of pivoted arms biased toward each other and engaging the plunger flange and each arm has an anti-siphon flange for engaging the plunger flange to restrain the flange from movement in the first direction;
   a detector coupled with the pushing surface to detect the presence of the plunger flange within the predetermined distance and to provide a detector signal indicating the presence of the plunger, the detector having a detection range large enough to detect the presence of all of the plunger flanges of the different sizes;
   a spring coupled to the plunger retainer to bias the plunger retainer into contact with the plunger flange; and
   a processor which receives the detector signal and provides an alarm in the event that the detector signal indicates a syringe plunger not present.

15. The system of claim 14 wherein the arms are curved in shape, the curve selected so that the arms will apply lateral force to all of the plunger flanges of the selected plungers.

16. A plunger driver system for engaging plungers of different sizes, each plunger having a plunger flange wherein each of the selected plungers forms a part of a syringe, each syringe having a barrel into and out of which the plunger moves, each plunger flange having an inner side facing the syringe barrel and an outer side, the plunger driver system moving the syringe plunger into the syringe barrel in an operation mode, the plunger driver system comprising:
   a pushing surface adapted to press against the outer side of the plunger flange to move the plunger into the barrel of the syringe during the operation mode;
   a plunger retainer adapted to engage the inner side of the plunger flange applying lateral force thereto and physically retain the flange within a predetermined distance from the pushing surface, the retainer also adjusting itself to the size of the flange;
   a detector coupled with the pushing surface to detect the presence of the plunger flange within the predetermined distance between the pushing surface and the plunger retainer during the operation mode and to provide a detector signal indicating the presence of the plunger, the detector having a detection range large enough to detect the presence of all of the plunger flanges of the different sizes when located between the pushing surface and the plunger retainer;
   a spring coupled to the plunger retainer to bias the plunger retainer into contact with the plunger flange;
   a processor which receives the detector signal and continuously monitors the detector signal during the operation mode and provides an alarm in the event that the detector signal indicates a syringe plunger not present during the operation mode;
   a cradle fixed in position and disposed to engage the barrels of each of the syringes, the cradle having a first surface and a barrel retainer, the first surface and the retainer being disposed to engage the syringe barrel between them; and
   the shape of the first surface and the shape of the retainer being selected to engage all syringes such that the longitudinal centerlines of all syringe plungers intersect the pushing surface along a common centerline.

17. The system of claim 16 wherein the first surface and the barrel retainer form a V-shape between them having an included angle of approximately 96 degrees.

18. The system of claim 16 further comprising a barrel clamp mounted above the cradle and biased toward the cradle to press against the barrel of syringe and hold the syringe in a fixed position in the cradle, the mounting position of the barrel clamp selected to provide downward force to all of the selected syringes.

19. The plunger driver system of claim 16 wherein the plunger retainer comprises at least one pivotally mounted arm that includes an anti-siphoning flange for engaging the inner surface of the plunger flange of the mounted syringe to retain the plunger within the predetermined distance of the pushing surface, the arm pivoting in one direction into engagement with the plunger flange and pivoting in another direction away from the flange into a disengaged position.

20. The plunger driver system of claim 19 wherein the plunger retainer comprises a second pivotally mounted arm for engaging the plunger flange of the mounted syringe, the arm pivoting in one direction into engagement with the plunger flange and pivoting in another direction away from the flange into a disengaged position.

21. The plunger driver system of claim 16 wherein the processor controls the pushing surface to stop pressing against the outer side of the plunger flange upon the processor providing an alarm.

22. The plunger driver system of claim 16 wherein the detector comprises:

a contact device mounted to the pushing surface for movement therewith, said contact device movable to a first contact position in contact with a plunger flange in response to said plunger flange being located between the pushing surface and the plunger retainer and movable to a second noncontact position when no plunger flange is located between the pushing surface and the plunger retainer;

a flag mounted to the contact device and moving therewith, the flag movable to a first flag position in response to the contact device being located in the first contact position and a second flag position in response to the contact device being located in the second noncontact position; and wherein the detector comprises a detecting device responsive to the position of the flag to provide the detector signal that indicates the position of the flag; and wherein the detecting device is mounted at the second flag position of the flag and during the operation mode, the processor tests the detecting device for correct operation thereby verifying that the detecting device has not failed.

23. The plunger driver system of claim 22 wherein the detecting device provides an optical beam and is mounted so that when the flag is in the first flag position, the flag does not break the optical beam;

wherein the processor pulses the optical beam when the flag is in the first flag position and provides an alarm if the detecting device does not detect the pulsed optical beam.

24. A plunger driver system for engaging plungers of different sizes, each plunger having a plunger flange, said plunger driver being connected to a lead screw driving mechanism which comprises a lead screw, a driver device coupled to the lead screw for movement along the lead screw in response to rotary motion of the lead screw and a bias mechanism for biasing the driver device into contact with the lead screw, comprising:

a pushing surface which is adapted to press against the plunger flange to move it in a first direction;

a plunger retainer adapted to engage the plunger flange applying lateral force thereto and retaining the flange within a predetermined distance from the pushing surface, the retainer also adjusting itself to the size of the flange wherein:

the plunger retainer comprises a pair of pivoted arms biased toward each other and engaging the plunger flange, the arms are curved in shape, the curve selected so that the arms will apply lateral force to all of the plunger flanges of the selected plungers; and each arm has an anti-siphon flange for engaging the plunger flange to restrain the flange from movement in the first direction;

a detector coupled to the pushing surface to detect the presence of the plunger flange within the predetermined distance and to provide a detector signal indicating the presence of the plunger, the detector having a range of detection large enough to detect the presence of all of the plunger flanges of the plungers of different sizes;

a spring coupled to the plunger retainer to bias the plunger retainer into contact with the plunger flange and which is independent from the screw drive bias mechanism;

an activating lever which is connected to the lead screw drive mechanism to oppose the bias mechanism of the screw drive mechanism and the lever is also connected to the plunger retainer to disengage the plunger retainer from the plunger flange; and a processor which receives the detector signal and provides an alarm in the event that the detector signal indicates a syringe plunger not present.

25. The system of claim 24 wherein the detector comprises:

a button mounted in the pushing surface;

a spring which biases the button outward into contact with the plunger flange;

a flag mounted to the button which moves with the button; and an optical sensor positioned to detect the flag to determine the position of the button and thereby determine the presence of a plunger flange.

* * * * *